United States Patent [19]

Andrási et al.

[11] Patent Number: 5,204,343
[45] Date of Patent: Apr. 20, 1993

[54] 5H-BENZODIAZEPIN DERIVATIVE

[75] Inventors: Ferenc Andrási; Péter Botka; Katalin Goldschmidt née Horváth; Tamás Hámori; Gyula Horváth; Jenő Kőrösi; Imre Moravcsik; Márta Rusz née Pátfalusi; Éva Tomori née Joszt; Gábor Zólyomi, all of Budapest, Hungary

[73] Assignee: Egis Gyógyszergyár, Budapest, Hungary

[21] Appl. No.: 776,771

[22] Filed: Oct. 17, 1991

[30] Foreign Application Priority Data

Oct. 17, 1990 [HU] Hungary .................... 6469/90

[51] Int. Cl.$^5$ .................... C07D 243/00; A61K 31/55
[52] U.S. Cl. .................... 514/221; 540/567
[58] Field of Search .................... 540/567; 514/221

[56] References Cited

U.S. PATENT DOCUMENTS 4,322,346  3/1982  Kőrösi et al. .................... 540/567

Primary Examiner—Mukund J. Shah
Assistant Examiner—Philip I. Datlow
Attorney, Agent, or Firm—Beveridge, DeGrandi, Weilacher & Young

[57] ABSTRACT

The invention relates to the new 1-(3-chlorophenyl)-4-hydroxymethyl-7,8-dimethoxy-5H-2,3-benzodiazepine of formula (I)

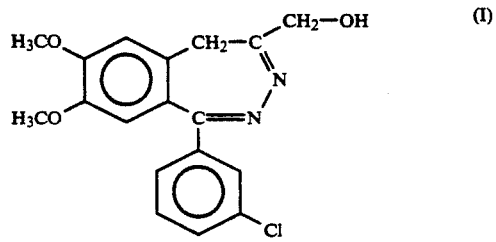

and pharmaceutically acceptable acid addition salts thereof, furthermore to a process for preparing these compounds.

The compounds according to the invention possess valuable anxiolytic, antiaggressive and antidepressant effects and have at the same time favorable acute toxicity values, so they can be used to advantage in therapy.

3 Claims, No Drawings

5H-BENZODIAZEPIN DERIVATIVE

This invention relates to a new 5H-2,3-benzodiazepine derivative, the acid addition salts thereof, pharmaceutical compositions comprising the same and process for preparing them. The invention covers also the use of the said 5H-2,3-benzodiazepine derivative for the treatment of diseases.

The aim of the present invention was to provide new and pharmaceutically effective 5H-2,3-benzodiazepine derivatives possessing central nervous activity exceeding not only that of Grandaxin but proving at least as strong as that of girisopam, and being at the same time superior to it in respect of the therapeutical index. Grandaxin [tofisopam, 1-(3,4-dimethoxyphenyl)-4-methyl-5-ethyl-7,8-dimethoxy-5H-2,3-benzodiazepine] is a commercially available anxiolytic, till now the only one among the 5H-2,3-benzodiazepine derivatives (U.S. Pat. No. 3,736,315), while girisopam [1-(3-chlorophenyl)-4-methyl-7,8-dimethoxy-5H-2,3-benzodiazepine] is a newer analogue of grandaxin, which is five times more effective than the latter and is under clinical trials (U.S. Pat. No. 4,322,346).

It has been found that the compound of formula (I)

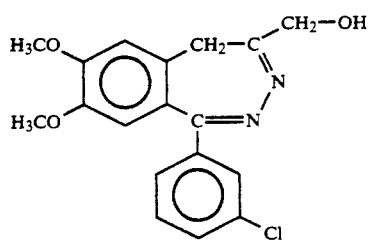

and the pharmaceutically acceptable acid addition salts thereof meet the above requirements, as they exert as strong anxiolytic, antiaggressive and antidepressant effects as girisopam and do not show muscle relaxant and anticonvulsive effects either, but their acute toxicity is superior.

On the basis of the above characteristics the compound of formula (I) can be considered as an excellent psychotropic compound.

According to an aspect of the present invention there is provided a new 5H-2,3-benzodiazepine derivative of formula (I), namely 1-(3-chlorophenyl)-4-hydroxymethyl-7,8-dimethoxy-5H-2,3-benzodiazepine. The pharmaceutically acceptable acid addition salts of the said compound are also provided.

According to another aspect of the present invention there is provided a process for the preparation of the new 5H-2,3-benzodiazepine derivative of formula (I) and pharmaceutically acceptable acid addition salts thereof, which comprises a₁) reacting dl-3-(3,4-dimethoxyphenyl)-propane-1,2-diol of formula (II)

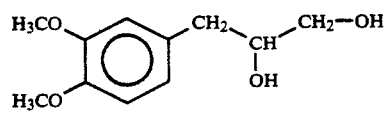

with 3-chlorobenzaldehyde acylating the new isochromane derivative of formula (III)

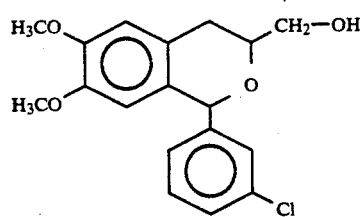

thus obtained with an aliphatic carboxylic acid comprising 1 to 4 carbon atom(s) or with a reactive derivative thereof, oxidating the acylated isochromane derivative thus obtained with chromic acid, reacting the new 1,5-diketone derivative of the general formula (IV)

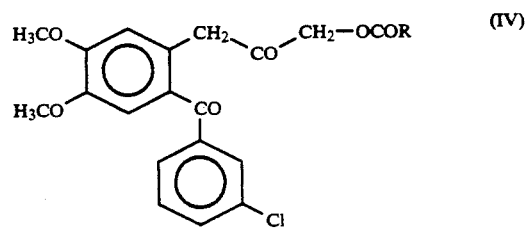

thus obtained—wherein R stands for $C_{1-4}$ alkyl -, directly or after having been converted into the corresponding 2-benzopyrilium salt, with hydrazine hydrate and, if desired, converting the base of formula (I) thus obtained into a pharmaceutically acceptable acid addition salt; or a₂) acylating the new isochromane derivative of formula (III) with a carboxylic acid comprising 1 to 4 carbon atom(s) or with a reactive derivative thereof, oxidating the acylated isochromane derivative thus obtained with chromic acid, reacting the new 1,5-diketone derivative of the general formula (IV) thus obtained—wherein R stands for $C_{1-4}$ alkyl -, directly or after having been converted into the corresponding 2-benzopyrilium salt, with hydrazine hydrate and, if desired, converting the base of formula (I) thus obtained into a pharmaceutically acceptable acid addition salt; or a₃) reacting a new 1,5-diketone derivative of the general formula (IV)—wherein R stands for $C_{1-4}$ alkyl -, directly or after having been converted into the corresponding 2-benzopyrilium salt, with hydrazine hydrate and, if desired, converting the base of formula (I) thus obtained into a pharmaceutically acceptable acid addition salt.

According to a preferred embodiment of process variant a₁) dl-3-(3,4-dimethoxyphenyl)-propane-1,2-diol of formula (II), a known compound, is used as starting material, which is reacted with 3-chlorobenzaldehyde in benzene, in the presence of concentrated hydrochloric acid catalyst diluted with water. The new isochromane derivative of formula (III) thus obtained is protected by acylation carried out with an aliphatic carboxylic acid comprising 1 to 4 carbon atom(s) or with a reactive derivative thereof (acid chloride, acid anhydride). It is particularly preferred to perform the acylation with hot acetic anhydride. The protected isochromane derivative is converted into a new 1,5-diketone derivative of the general formula (IV) by oxidation carried out with chromic acid. The said oxidation reaction is preferably performed with Jones reagent in analogous manner [Ber. Deut. Chem. Ges. 75, 891 (1942); J.

Am. Chem. Soc. 72, 1118 (1950); Acta Chim. Acad. Sci. Hung. 2, 231 (1952), 41, 451 (1964); Hungarian patent specification No. 194,529]. Finally, the new 1,5-diketone derivative of the general formula (IV) thus obtained is reacted with 3 to 7 molar equivalents of 98 to 100% by mass hydrazine hydrate in a 99.5% ethanol solution at room temperature and, if desired, the base of formula (I) thus obtained is converted into an acid addition salt by methods known per se.

According to another preferred embodiment of process variant $a_1$) the reaction is carried out as specified above except that the new 1,5-diketone derivative of the general formula (IV) is first converted into the corresponding 2-benzopyrilium salt by methods known per se and then reacted with hydrazine hydrate. Reactions of such kind are published in British patent specifications Nos. 1,202,579 and 2,034,706.

Further embodiments of the process according to the invention are the reactions starting from the new isochromane derivative of formula (III) or from the new 1,5-diketone derivatives of the general formula (IV) [reactions according to process variants $a_2$) and $a_3$)]. These reactions are preferably carried out as specified in connection with process variant $a_1$).

The compound of formula (II) [dl-3-(3,4-dimethoxyphenyl)-propane-1,2-diol] used as starting compound for process variant $a_1$) and the preparation thereof are known from the literature [J. Am. Chem. Soc. 75, 4291 (1953); Canad. J. Chem. 33, 102 (1955); J. Chem. Soc. 4252 (1956)].

The starting compounds of process variants $a_2$) and $a_3$) are known derivatives and can be produced as described in the Examples.

The process according to the invention results in the compound of formula (I) in the form of a base. The acid addition salts thereof are preferably prepared by dissolving the base in a suitable solvent, such as methanol, isopropanol or diethyl ether, and adding an appropriate acid or a solution thereof in an inert solvent to it. The salts can be separated by direct filtration or optionally by distilling off the solvent.

As it has already been mentioned, the new 5H-2,3-benzodiazepine derivative of formula (I) exerts a highly significant central nervous activity and its toxicity values are very favourable. The results of the most important pharmacological tests are shown as follows:

Behaviour Test on Mice

The effects of the compound of formula (I) and the reference compound (girisopam) were examined by the method of Irwin [Psychopharmacol. 13, 222 (1968)]. The results are given in Table I.

TABLE 1

| Compound | Dose mg/kg | After 60 | 120 minutes | 180 |
|---|---|---|---|---|
| Compound of formula (I) | 100 i.p. | SMA ↓ | SMA ↓ | SMA ↓ |
|  | 200 p.o. | SMA ↓ | SMA ↓ | SMA ↓ |
| Girisopam (reference compound) | 100 i.p. | SMA ↓ | SMA ↓ | SMA ↓ |
|  | 200 p.o. | SMA ↓ | SMA ↓ | SMA ↓ |

SMA = spontaneous motor activity

According to the above test data the compound of formula (I) decreases the spontaneous motor activity on mice to the same degree as the reference compound.

Narcosis Potentiating Effect on Mice

The prolongation of the narcosis time was related to the sleeping time of the control group treated with a 50 mg/kg i.v. dose of hexobarbital-Na. The test compound was administered 30 minutes after this treatment. The results are summarized in Table II.

TABLE II

| Compound | Dose mg/kg p.o | Prolangation % |
|---|---|---|
| Compound of formula (I) | 50 | 444 |
|  | 25 | 232 |
|  | 12.5 | 145 |
| Girisopam | 50 | 392 |
|  | 25 | 305 |

From the data of the above Table it can be seen that the activity of the compound of formula (I) in p.o. doses 25 mg/kg and 50 mg/kg is practically as significant as that of the reference compound (girisopam) or even superior.

Antiaggressive Effect on Mice

The antiaggressive effect was examined by the method of Tedeschi et al. (the so-called "fighting behaviour" test) [J. Pharm. Exp. Ther. 25, 28 (1959)]. The results are shown in Table III.

TABLE III

| Compound | $ED_{50}$ | Confidence limit |
|---|---|---|
| Compound of formula (I) | 13.8 | (9.7–20.0) |
| Girisopam | 16.0 | (12.4–20.6) |

From the data of Table III it can be established that on this test the potency of the compound of formula (I) is similar or somewhat superior to that of the reference compound (girisopam).

Anxiolytic Effect on Rats

The anxiolytic effect was investigated according to the so-called "lick-conflict" test of Vogel [Psychopharmacol. 21, 1 (1971)]. Time of pretreatment: 30 minutes. The results are given in Table IV.

TABLE IV

| Compound | Dose mg/kg i.p. | Numbers of shocks tolerated | Significance |
|---|---|---|---|
| Vehicle | — | 5.7 ± 0.6 |  |
| Compound of formula (I) | 50 | 13.8 ± 3.7 | $p < 0.05$ |
| Vehicle | — | 5.1 ± 0.9 |  |
| Girisopam | 50 | 19.0 ± 2.3 | $p < 0.01$ |

According to the above tests both the compound of formula (I) and the reference compound cause a significant increase on the number of tolerated shocks in the same dose.

Acute Toxicity

The experiments were carried out on male mice belonging to the CFLP strain (body weight: 20–22 g) and on male rats belonging to the CFY strain. After a single treatment with the test compounds the animals were observed for 14 days. The $LD_{50}$ values were determined with the aid of the method of Lichtfield and Wilcoxon [J. Pharmacol. Exp. Ther. 96, 99 (1949)]. The compounds were suspended in 2 to 5% Tween 80. The animals were treated in volumes of 0.1 ml/10 g (mice) and 0.5 ml/100 g (rats).

The results are summarized in Table V.

TABLE V

| Compound | Animal | Method of treatment | $LD_{50}$ mg/kg | Confidence interval |
|---|---|---|---|---|
| Compound of formula (I) | mouse | i.p. | 1309 | (1074–1595) |
| | mouse | p.o. | >2000 | |
| | rat | i.p. | >1500 | |
| Girisopam | mouse | i.p. | 330 | (289–376) |
| | mouse | p.o. | 1250 | (1106–1412) |
| | rat | i.p. | 670 | (567–791) |

From the above Table it can be seen that the acute toxicity of the compound of formula (I) is considerably more favourable on both kinds of animals than that of the reference compound.

Summing up it can be established that according to the pharmacological experiments the spectrum of activity and the potency of the new 5H-2,3-benzodiazepine derivative of formula (I) are as favourable as those of the reference compound (girisopam). In respect of the therapeutical index, however, the new derivative is more favourable than the reference compound, consequently both the base of formula (I) and the pharmaceutically acceptable acid addition salts thereof can be used in the therapy for the treatment of disorders of the central nervous system.

According to a further aspect of the present invention there are provided pharmaceutical compositions comprising as active ingredient the compound of formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatin capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potatoe starch, talc, magnesium carbonate, magnesium stearate, calcium carbonate, stearic acid or the salts therof, etc. can be used. As carrier for the soft gelatine capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers, etc.

The daily dose of the compound of formula (I) can vary within wide ranges depending on several factors, e.g. on the activity of the active ingredient, the patient's condition and age, the severity of the disease, etc. The oral dose is generally 1 to 1000 mg/day, preferably 100 to 300 mg/day. It has to be stressed that these dose values are only of informative character and the administered dose must always be determined by the physician therapeutist.

According to a further aspect of the present invention there is provided the use of the compound of formula (I) or pharmaceutically acceptable salts thereof for the preparation of pharmaceutical compositions having particularly central nervous activity.

According to a still further aspect of the present invention there is provided a method of anxiolytic, antiaggressive and/or antidepressant treatment, which comprises administering to the patient an effective amount of the compound of formula (I) or a pharmaceutically acceptable salt thereof.

The invention is further illustrated by the following Examples of non-limiting character.

EXAMPLE 1

1-(3-Chlorophenyl)-4-hydroxymethyl-7,8-dimethoxy-5H-2,3-benzodiazepine (I)

6.7 g (17.3 mmoles) of 2-(3-acetoxyacetonyl)-3'-chloro-4,5-dimethoxybenzophenone [(IV), $R=CH_3$] are suspended in 70 ml of 99.5% ethanol, then 5.2 1 (104 mmoles) of 100% hydrazine hydrate are added under stirring. The reaction mixture is stirred at room temperature for 72 hours, treated with activated carbon, filtered and 82 ml of distilled water are added to the filtrate. Then 4 ml of glacial acetic acid are dropped to the pale yellow solution under cooling with ice-cold water. Upon scratching crystals get separated. The suspension is kept overnight at 1° to 5° C., filtered, washed five times with 5 ml of ice-cold 50% ethanol solution each and the product is dried at a temperature between 80° and 100° C. Thus 4.64 g of crude product are obtained.

M.p.: 158°–160° C. (decomp.)

Yield: 77.8%

Analysis for the formula $C_{18}H_{17}ClN_2O_3$ (m.w.==344.807)

| calculated: | C % 62.70 | H % 4.97 | N % 8.12 |
|---|---|---|---|
| found: | C % 62.77 | H % 4.99 | N % 8.00. |

The active ingredient content of the crude product is at least 97%. This product can be further purified by recrystallization from a 99.5% ethanol solution or by column chromatography (absorbent: 0.063–0.2 mm Kieselgel 60; eluent: 4:1 mixture of ethyl acetate and benzene). The purified base of formula (I) decomposes at 159°–161° C. The hydrochloride salt decomposes at 193°–195° C., the methanesulfonate salt decomposes at temperatures exceeding 186° C.

The new 2-(3-acetoxyacetonyl)-3'-chloro-4,5-dimethoxybenzophenone used as starting substance can be prepared as specified below:

Step 1

1-(3-Chlorophenyl)-3-hydroxymethyl-6,7-dimethoxyisochromane (III)

15.64 g (73.6 mmoles) of dl-3-(3,4-dimethoxyphenyl)-propane-1,2-diol (II) are dissolved in 200 ml of benzene. 8.03 ml (73.6 mmoles) of 3-chlorobenzaldehyde and 4.6 ml (56 mmoles) of concentrated hydrochloric acid are added to the solution and the reaction mixture is stirred for 5 hours at room temperature. The solution is then evaporated in vacuo, the oily residue is dissolved in 200 ml of 99.5% ethanol, clarified while hot, filtered and the filtrate is evaporated in vacuo. Thus 23.19 g (94%) of crude product are obtained in oily form, which can be used for the further reaction steps without purification (the purity of the product exceeds 95%).

Step 2

2-(3-Acetoxyacetonitrile)-3'-chloro-4,5-dimethoxybenzophenone [(IV), R=CH3[

23.19 g (69.2 mmoles) of 1-(3-chlorophenyl)-3-hydroxymethyl-6,7-dimethoxyisochromane are dissolved in 100 ml of acetic anhydride. The reaction mixture is boiled for 3 hours under reflux, then it is evaporated in vacuo, and three times 50 ml each of 99.5% ethanol are distilled off the residual gum in vacuo. Thus 24.8 g of crude 1-(3-chlorophenyl)-3-acetoxymethyl-6,7-dimethoxyisochromane are obtained. Yield: 95%.

24.0 g (63.6 mmoles) of the above crude product are dissolved in 240 ml of acetone, and 47.6 ml of Jones reagent containing 127 mmoles of chromic acid are dropped to it within 30 minutes under stirring, while the inner temperature is kept between 10 and 15° C. The reaction mixture is stirred for further 3 hours. Upon diluting with 800 ml of distilled water crystals begin to separate The mixture is allowed to stand overnight, the separated crystals are filtered, washed three times with 100 ml each of ice-cold distilled water and dried. Thus 20.43 g of product are obtained. M.p.: 98°-102° C. (at temperature exceeding 90° C. it shrinks). The crude product is recrystallized from 80 ml of 99.5% ethanol. Thus 12.0 g of the desired compound are obtained. Yield: 48.7%, m.p.: 104°-105° C.

EXAMPLE 2

Pharmaceutical Composition

Tablets or divided tablets containing 50 mg of 1-(3-chlorophenyl)-4-hydroxymethyl-7,8-dimethoxy-5H-2,3-benzodiazepine and having the following composition are prepared by known methods of the pharmaceutical industry.

| Component | Amount, mg/tablet |
|---|---|
| Active ingredient | 50 |
| Potato starch | 106 |
| Lactose | 300 |

-continued

| Component | Amount, mg/tablet |
|---|---|
| Polyvinylpyrrolidone | 12 |
| Magnesium stearate | 2 |
| Talc | 30 |

EXAMPLE 3

Pharmaceutical Composition

Tablets or dragées containing 25 mg of 1-(3-chlorophenyl)-4-hydroxymethyl-7,8-dimethoxy-5H-2,3-benzodiazepine and having the following composition are prepared by known methods of the pharmaceutical industry.

| Component | Amount, mg/tablet or dragée |
|---|---|
| Active ingredient | 25 |
| Potato starch | 43 |
| Lactose | 160 |
| Polyvinylpyrrolidone | 6 |
| Magnesium stearate | 1 |
| Talc | 30 |

What we claim is:
1. The new 1-(3-chlorophenyl)-4-hydroxymethyl-7,8-dimethoxy-5H-2,3-benzodiazepine or formula (I)

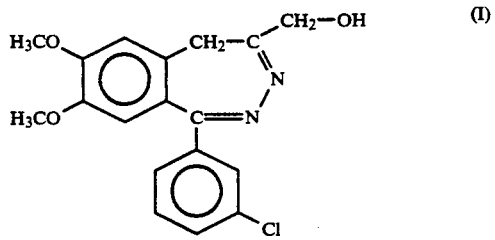

and pharmaceutically acceptable acid addition salts thereof.

2. A pharmaceutical composition comprising as active ingredient the compound of formula (I) as claimed in claim 1 or a pharmaceutically acceptable acid addition salt thereof in admixture with suitable inert solid or liquid pharmaceutical carriers.

3. A method of anxiolytic, antiaggressive and/or antidepressant treatment, which comprises administering to a patient in need thereof an effective amount of a compound of formula (I) as claimed in claim 1 or a pharmaceutically acceptable salt thereof.

* * * * *